United States Patent [19]

Bock et al.

[11] Patent Number: 5,206,234
[45] Date of Patent: Apr. 27, 1993

[54] BENZOLACTAM ANALOGS AS ANTAGONISTS OF CCK

[75] Inventors: Mark G. Bock, Hatfield; Roger M. Freidinger; Ben E. Evans, both of Lansdale, all of Pa.

[73] Assignee: Merck & Co., Inc., Rahway, N.J.

[21] Appl. No.: 718,075

[22] Filed: Jun. 20, 1991

Related U.S. Application Data

[63] Continuation-in-part of Ser. No. 602,031, Oct. 22, 1990, abandoned.

[51] Int. Cl.$^5$ .................... A61K 31/55; C07D 223/16
[52] U.S. Cl. .................... 514/213; 540/523; 546/157; 548/465; 548/438; 514/312; 514/414; 514/415
[58] Field of Search .................. 540/523; 546/157; 548/465, 438; 514/213, 312, 414, 415

[56] References Cited

U.S. PATENT DOCUMENTS 4,652,641  3/1987  Parsons ................ 540/523

FOREIGN PATENT DOCUMENTS 0166357  1/1986  European Pat. Off. ........... 540/523

OTHER PUBLICATIONS

Kobayashi et al., Chemical Abstracts, vol. 110, No. 15, Abstract No. 13508n, p. 699, Apr. 10, 1989.
Lotti, et al., Chemical Abstracts, vol. 110, No. 23, Abstract No. 205932s, p. 94, Jun. 5, 1989.

*Primary Examiner*—Robert T. Bond
*Attorney, Agent, or Firm*—Francis P. Bigley; Joseph F. DiPrima

[57] ABSTRACT

Benzolactam analogs of the formula:

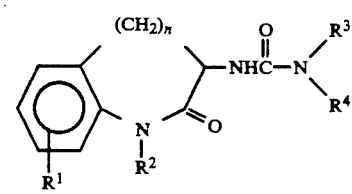

are disclosed which are antagonists of gastrin and cholecystokinin (CCK).

34 Claims, No Drawings

BENZOLACTAM ANALOGS AS ANTAGONISTS OF CCK

CROSS-REFERENCE

This is a continuation-in-part application of U.S. Ser. No. 602,031 filed on Oct. 22, 1990 now abandoned.

FIELD OF THE INVENTION

This invention relates to the discovery of Benzolactam Analogs of Formula I for use as antagonists of cholecystokinin (CCK) and gastrin when administered to animals, preferably humans.

BACKGROUND OF THE INVENTION

The Benzolactam analogs of formula I of this invention are useful in treating various diseases caused by an excess of CKK or gastrin. Cholecystokinins (CCK) and gastrin are structurally related neuropeptides which exist in gastrointestinal tissue and in the central nervous system (see, V. Mutt, *Gastrointestinal Hormones*, G. B. J. Glass, Ed., Raven Press, N.Y., p. 169 and G. Nission, ibid, p. 127.

The isolation of the 33-amino acid polypeptide, cholecystokinin (CCK-33), from porcine intestine, Mutt, V. et al., "Structure of Porcine Cholecystokininpancreozymin. 1. Cleavage with Thrombin and Trypsin", *European J. Biochem.* 6, 156, (1968), was followed by the discovery that it occurs in numerous molecular forms at various sites throughout the peripheral and central nervous systems, Larsson, L. et al., "Localization and Molecular Heterogeneity of Cholecystokinin in the Central and Peripheral Nervous System", Brain Res., 165, 201 (1979). In the mammalian brain the predominant fragments are the carboxy terminal octapeptide, H-Asp-Tyr($SO_3$H)-Met-Gly-Trp-Met-Asp-Phe-$NH_2$ (CCK-8s, $CCK_{26-33}$) and tetrapeptide CCK-4 ($CCK_{30-33}$).

The carboxy terminal octapeptide possesses the full biological profile of CCK, Dockray, G. J. et al., "Isolation, Structure and Biological Activity of Two Cholecystokinin Octapeptides from Sheep Brain", *Nature* 274, 711 (1978), and meets many anatomical and biochemical criteria which characterize a neurotransmitter, Vanderhaeghen, J. J. et al., "J. Neuronal Cholecystokinin", *Ann. N.Y. Acad. Sci.*, 448, (1985). The presence of high concentrations of CCK-8s in the mammalian CNS is complemented with findings of specific and high affinity membrane-bound CCK binding sites, Innis, R. B. et al., "Distinct Cholecystokinin Receptors in Brain and Pancreas", *Proc. Natl. Acad. Sci. U.S.A.*, 77, 6917 (1980).

Evidence that more than one form of CCK receptor might exist was first provided in 1980 by Innis and Snyder, Innis, R. B. et al., "Distinct Cholecystokinin Receptors in Brain and Pancreas", *Proc. Natl. Acad. Sci. U.S.A.*, 77, 6917 (1980). At present, CCK receptors have been differentiated into primarily two subtypes based on their affinity for CCK fragments and analogues, Innis, R. B. et al., "Distinct Cholecstokinin Receptors in Brain and Pancreas", *Proc. Natl. Acad. Sci. U.S.A.*, 77, 6917 (1980). The subsequent development of agents which discriminate between different CCK receptor types afforded further support for these assignments, Chang, R.S.L. et al., "Biochemical and Pharmacological Characterization of an Extremely Potent and Selective Nonpeptide Cholecystokinin Antagonist", *Proc. Natl. Acad. Sci. U.S.A.*, 83, 4923 (1986).

The CCK-A receptors, previously known as peripheral CCK receptors, are located in organs such as the pancreas, gallbladder, and colon. They exhibit high affinity for CCK-8s and a lower affinity for the corresponding desulphated fragment, CCK-8d, for CCK-4, and gastrin. Recent autoradiographic results have localized CCK-A receptors in the brain as well, Hill, D.R. et al., "Autoradiographic Localization and Biochemical Characterization of Peripheral Type CCK Receptors in Rat CNS Using Highly Selective Nonpeptide CCK Antagonists", *J. Neurosci.*, 7,2967 91987).

The majority of the CCK receptors in the brain are of the CCK-B type. These were previously designated as central CCK receptors. CCK-B receptors are widely distributed throughout the brain and display high affinity for CCK-8s, CCK-4, and pentagastrin, Hill, D.R. et al., "Autoradiographic Localization and Biochemical Characterization of Peripheral Type CCK Receptors in Rat CNS Using Hightly Selective Nonpeptide CCK Antagonists", *J. Neurosci,* 7, 2967 (1987).

In addition to the above mentioned CCK receptor subtypes is a third type, the stomach gastrin receptor, which appears to be closely related to the CCK-B receptor subtype, Beinfeld, M.C., "Cholecystokinin in the Central Nervous System; a Minireview", *Neuropeptides,* 3, 4111 (1983). The minimum fully potent CCK sequence at this receptor is CCK-4, Gregory, R. A., "A review of some Recent Development in the Chemistry of the Gastrins", *Biorg. Chem.,* 8,497 (1979).

A wide range of physiological responses has been attributed to CCK. In an effort to elucidate its biological roles, researchers have relied primarily on a collection of CCK—A antagonists which has been steadily supplemented and improved to now include very selective, high-affinity agents, Evans, B. E., "Recent Developments in Cholecystokinin Antagonist Research," *Drugs Future,* 14, 971 (1989). In addition to the their value as investigative tools, CCK antagonists retain considerable therapeutic potential, Gertz, B. J., "Potential Clinical Applications, of a CCK Antagonist in Cholecystokinin Antagonists," Alan R. Liss, Inc.: New York, pp. 327 (1988).

In recent years, interest in agonists and antagonists of CCK has been stimulated by the possible clinical application of such compounds, Silverman, M. A. et al., "Cholecystokinin Receptor Antagonists, a Review", Am. J. Gastroenterol, 82, 703, (1987). The discovery of the presence of CCK in the brain and its significance in relation to its modulation of dopaminergic functions, effects on satiety, its roles in nociception, in anxiety, and other brain functions, Vanderhaeghen, J. J., et al., "J. Neuronal Cholecystokinin", *Ann. N.Y. Acad. Sci.* 448 (1985) has understandably intensified the search for CCK-B selective agents. Since the relevant biologically active fragment, CCK-8s, has a half-life of less than 1 hour, Deschodt-Lanckman, K., et al., "Degradation of Cholecystokinin-like Peptides by a Crude Rat Brain Synaptosomal Fraction: a Study by High Pressure Liquid Chromatography", *Reg. Pept.,* 2, 15 (1981), implicit in the development of candidates for clinical use are criteria of high potency, selectivity, long in-vivo duration, oral bioavailability, and capability of penetrating the blood-brain barrier. These are strict prerequisites, given the tenuous stature of peptides as drugs, Veber, D. F., et al., "The Design of Metabolically-stable Peptide Analogs", *Trends Neurosci.* 8, 392 (1985).

Nevertheless, by employing stratagems which stabilize peptide structures, advances have been made toward developing highly potent and selective peptidal CCK-B receptor ligands Charpentier, B. et al., "Cyclic Cholecystokinin Analogues with High Selectivity for Central Receptors". *Proc. Natl. Acad. Sci. U.S.A.*, 85, 1968, (1988). Analogues are now available which have proven resistant to enzymatic degradation Charpentier, B. et al., "Enzyme-resistant CCK Analogs with High Affinities for Central Receptors", *Peptides* 9 835 (1988). Despite favorable receptor binding profiles, this class of compounds fails to meet previously cited key requirements which characterize a drug candidate. In response, researchers have turned to non-peptide compounds which offer a broader range of structure and physicochemical properties.

It is, therefore, an object of the present invention to provide antagonists of CCK and gastrin. If an antagonist compound could be prepared which would bind with the cell surface receptor of CCK or gastrin with equal or greater affinity then the naturally occuring CCK or gastrin, then the antagonist compounds of this invention could be used to block the effect of CCK and gastrin.

Another object of the present invention is to provide novel CCK and gastrin antagonist compounds which are useful in the treatment of panic disorder or anxiety disorder, treatment of oncologic disorders, controlling pupil constriction in the eye, treating pain or inducing analgesia or preventing a withdrawal response produced by treatment or abuse of drugs or alcohol. Other objects of the present invention are to provide methods of inhibiting the action of CCK and gastrin through the administration of novel benzolactam analog compounds. The above and other object are accomplished by the present invention in the manner more fully described below.

SUMMARY OF THE INVENTION

The present invention provides benzolactam analogs of the formula:

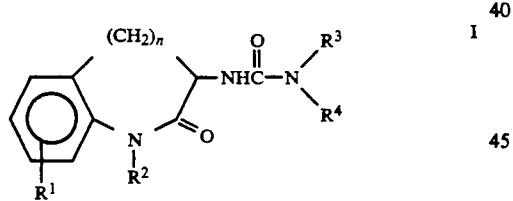

for use as antagonists of CCK and gastrin and are useful in the treatment of panic disorder or anxiety disorder, treatment of oncologic disorders, controlling pupil constriction in the eye, treating pain or inducing analgesia or preventing a withdrawal response produced by treatment or abuse of drugs or alcohol. The above-mentioned compounds can be used in a method of acting upon a CCK and/or gastrin receptor which comprises administering a therapeutically effective but non-toxic amount of such compound to an animal, preferably a human. A pharmaceutical composition comprising a pharmaceutically acceptable carrier and, dispersed therein, an effective but non-toxic amount of such compound is another aspect of this invention.

DETAILED DESCRIPTION OF THE INVENTION

Benzolactam analogs of Formula I are useful in a method of antagonizing the binding of CCK to CCK receptors or antagonizing the binding of gastrin to gastrin receptors, and are illustrated by compounds having the formula:

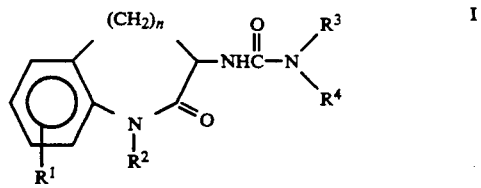

wherein:
$R^1$ is H, halo, hydroxy, nitro, amino, cyano, $C_1$–$C_8$-alkyl, $C_1$–$C_4$-alkylamino, $C_1$–$C_4$-alkoxy;

$R^2$ is unsubstituted or mono-, di-, or trisubstituted $C_1$–$C_8$-straight- or branched-alkyl, where the substituents are selected from the group consisting of $C_1$–$C_4$-alkylthio, $C_1$–$C_4$-alkyloxy, $C_1$–$C_4$-alkylamino, unsubstituted or mono-, di-, or trisubstituted phenyloxy or naphthyloxy unsubstituted or mono-, di-, or trisubstituted phenylthio or napthylthio, unsubstituted or mono-, di-, or trisubstituted phenyl or naphthyl, and unsubstituted or mono-, di-, or trisubstituted hetero-$C_3$–$C_9$-aryl, the one-to-three heteroatoms in the hetero-$C_3$–$C_9$-aryl being selected from O, S and N atoms, and the substituents on the phenyloxy or naphthyloxy, the phenylthio or naphthylthio, the phenyl or naphthyl and the hetero-$C_3$–$C_9$-aryl being selected from $C_1$–$C_8$-straight- or branched-alkyl, hydroxy, $C_1$–$C_4$-alkoxy, halo, nitro, amino, $C_1$–$C_4$-alkylthio or mono- or di-$C_1$–$C_4$-alkylamino; substituted carbonyl-$C_1$–$C_4$-alkyl, which carbonyl group is substituted with hydroxy, $C_1$–$C_8$-straight- or branched-alkoxy, $C_1$–$C_8$-straight- or branched-alkyl, unsubstituted or mono-, di-, or trisubstituted phenyl or naphthyl, unsubstituted or mono-, di-, or trisubstituted phenyl or naphthyl $C_1$–$C_8$-alkyl, and unsubstituted or mono-, di-, or trisubstituted phenyl or naphthyl-$C_1$–$C_4$alkoxy, where the substituents on the phenyl or naphthyl, the phenyl or naphthyl-$C_1$–$C_8$-alkyl or the phenyl or naphthyl-$C_1$–$C_4$-alkoxy are selected from the groups consisting of hydroxy, $C_1$–$C_8$-straight- or branched-alkyl, $C_1$–$C_4$-alkoxy, halo, cyano, nitro, amino, $C_1$–$C_4$-alkylthio, and mono- or di-$C_1$–$C_4$-alkylamino, or $NR^6R^7$, where $R^6$ and $R^7$ are independently selected from hydrogen, $C_1$–$C_6$-straight- or branched-alkyl, unsubstituted or mono-, di-, or trisubstituted-carboxy-$C_1$–$C_8$-straight- or branched-alkyl, or unsubstituted or mono-, di-, or trisubstituted-carboxamido-$C_1$–$C_8$-straight-or branched-alkyl, wherein the substituents on the carboxy-$C_1$–$C_8$-straight-or branched-alkyl or on the carboxamido-$C_1$–$C_8$-straight-or branched-alkyl are selected from the group consisting of unsubstituted or mono-, di-, or trisubstituted phenyl or naphthyl, unsubstituted or mono-, di- or trisubstituted phenyl or naphthyl-$C_1$–$C_8$-alkyl, unsubstituted or mono-, di-, or trisubstituted phenyl or naphthyl-1$C_{10}$-aryl-$C_{10}$-aryl-$C_1$–$C_4$-alkoxy, where the substituents on the phenyl or naphthyl, $C_1$–$C_8$-alkyl or the phenyl or naphthyl-$C_1$–$C_4$-alkoxy are selected from the group consisting of hydroxy, $C_1$–$C_8$-straight- or branched-alkyl, $C_1$–$C_4$-alkoxy, halo, nitro, cyano, amino, $C_1$–$C_4$-alkylthio, and mono- or di-$C_1$–$C_4$-alkylamino;

$R^3$ and $R^4$ are independently $R^5$ or in combination with the N of the $NR^3R^4$ group form an unsubstituted or mono- or disubstituted saturated or unsaturated, 4–7 membered heterocyclic ring, where the substituents are selected from the group consisting of hydroxy, $C_1$–$C_8$-straight- or branched alkyl, $C_1$–$C_4$ alkoxy, halo, nitro, amino, cyano, $C_1$–$C_4$-alkylthio and mono- or di-$C_1$–$C_4$-alkyamino or benzofused 4–7 membered heterocyclic ring;

$R^5$ is is unsubstituted or mono-, di- or trisubstituted phenyl or naphthyl, where the substituents are selected from the group consisting of $C_1$–$C_8$-straight- or branched-alkyl, hydroxy, $C_1$–$C_4$-alkoxy, halo, nitro, amino, cyano, $C_1$–$C_4$-alkylthio and mono- or di-$C_1$–$C_4$-alkylamino; unsubstituted or mono-, di- or trisubstituted heteroaryl, and the substituents are selected from the group consisting of $C_1$–$C_8$-straight- or branched-alkyl, hydroxy, $C_1$–$C_4$-alkoxy, halo, nitro, amino, cyano, $C_1$–$C_4$-alkylthio and mono- or di-$C_1$–$C_4$- alkylamino; unsubstituted or mono-, di- or trisubstituted heteroaryl-$C_1$–$C_8$-straight- or branched-alkyl, and the substituents are selected from the group consisting of $C_1$–$C_8$-straight- or branched-alkyl, hydroxy, $C_1$–$C_4$-alkoxy, halo, nitro, amino, cyano, $C_1$–$C_4$-alkylthio and mono- or di-$C_1$–$C_4$-alkylamino; $C_3$–$C_{10}$-cycloalkyl; $C_3$–$C_{10}$-cycloalkyl-$C_1$–$C_4$-alkyl; $C_1$–$C_6$-straight- or branched-alkyl-Q-$(CH_2)m$, where m is 2 to 4 and Q is O, S, SO, $SO_2$, —HC=CH—, or substituted amino, wherein the substituent is hydrogen, $C_1$–$C_8$-straight- or branched-alkyl, unsubstituted or mono-, di- or trisubstituted $C_6$- or $C_{10}$-aryl, unsubstituted or mono-, di- or trisubstituted heteroaryl, unsubstituted or mono-, di- or trisubstituted $C_6$- or $C_{10}$-aryl-$C_1$–$C_4$-alkyl, or unsubstituted or mono-, di- or trisubstituted heteroaryl where the substituents on the $C_6$- or $C_{10}$-aryl, the heteroaryl, the $C_6$- or $C_{10}$-aryl-$C_1$–$C_4$-alkyl, or the heteroaryl $C_1$–$C_4$-alkyl are selected from the group consisting of $C_1$–$C_8$-straight- or branched-alkyl, hydroxy, $C_1$–$C_4$alkoxy, halo, nitro, amino, $C_1$–$C_4$-alkyl-thio and mono- or di-$C_1$–$C_4$-alkylamino; or $C_9$–$C_{12}$-benzofused cycloalkyls;

n is 0–3;

or the optical isomers or pharmaceutically acceptable salts thereof.

Preferred compounds of this invention include the following compounds from the Examples as set forth below:

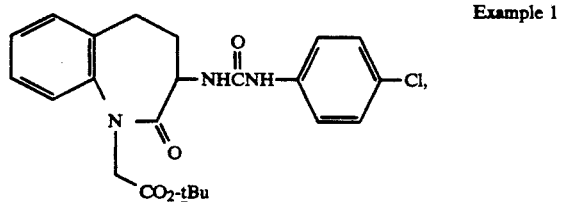
Example 1

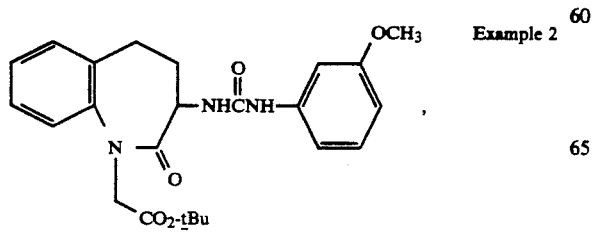
Example 2

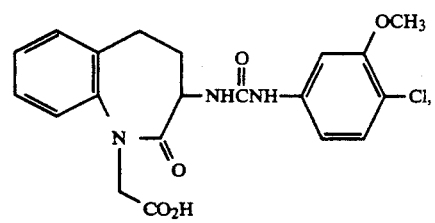
Example 3

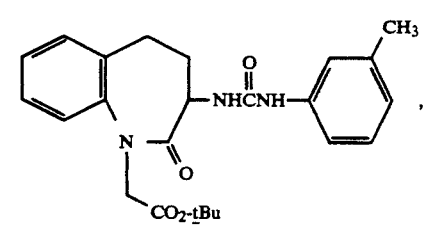
Example 4

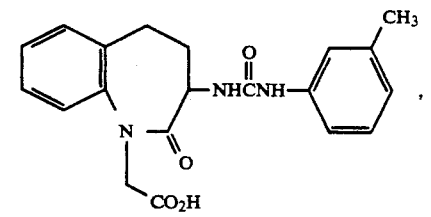
Example 5

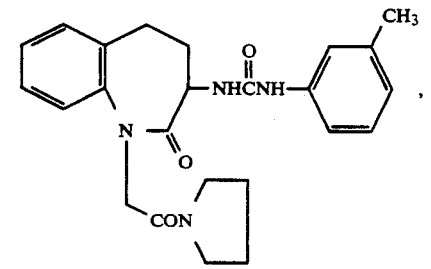
Example 6

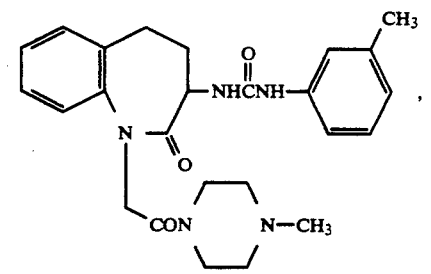
Example 7

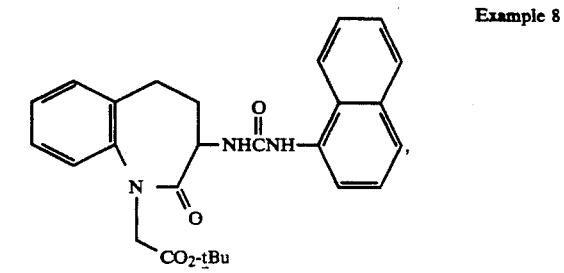
Example 8

-continued

Example 9
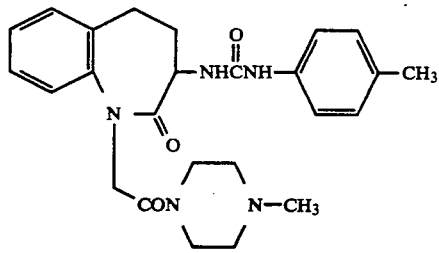

Example 10
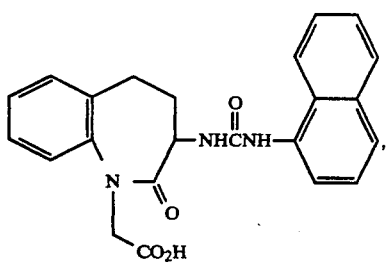

Example 11
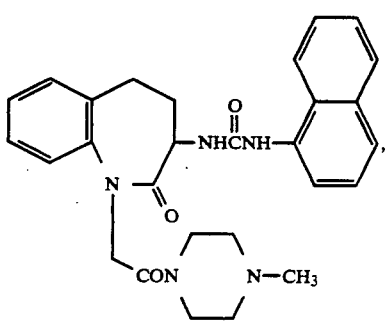

Example 12
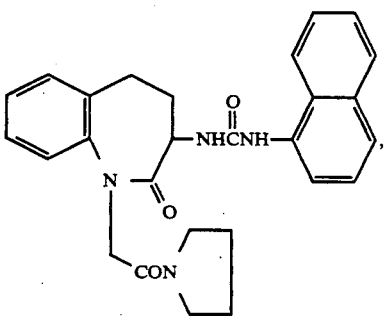

Example 13
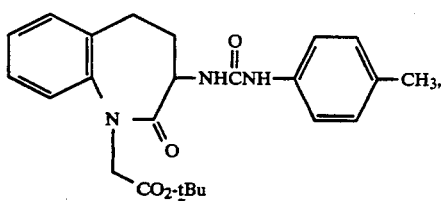

and

Example 14
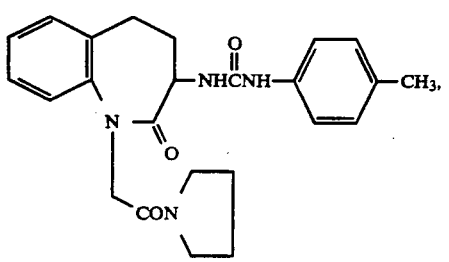

As used herein, the definition of each substituent when it occurs more than once in any structure, is intended to be independent of its definition elsewhere in the same structure. As used herein, halo is F, Cl, Br or I; alkyl and loweralkyl are each, unless otherwise indicated, 1–8 carbon straight or branched chain saturated, and includes methyl, ethyl, propyl, isopropyl, butyl, isobutyl, and t-butyl, pentyl, and hexyl; in loweralkoxy and loweralkylthio, the alkyl portion is loweralkyl is 1–4 carboxy, cycloalkyl consists of 3–7 carbons.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkaline or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I antagonize CCK and/or gastrin and are useful as pharmaceutical agents for animals, preferably for mammals, and most especially for humans, for the treatment and prevention of gastrointestinal disorders and central nervous system disorders.

Examples of such gastrointestinal disorders include ulcers, such as peptic and gastrointestinal ulcers, irritable bowel syndrome, gastroesophagenal reflux disease or excess pancreatic or gastrin secretion, acute pancreatitis, or motility disorders, Zollinger-Ellison snydrome, and antral and cell hyperplasia.

Examples of central nervous system disorders include central nervous system disorders caused by CCK interaction with dopamine, such as neuroleptic induced tardive dyskinesia, Parkinson's disease, schizophrenia, other psychosis or Gilles de la Tourette syndrome, and disorders of appetite regulatory systems.

The compounds of Formula I may further be useful in the treatment or prevention of additional central nervous system disorders including neurological and pyschiatric disorders. Examples of such central nervous system disorders include anxiety disorders and panic disorders, wherein CCK and/or gastrin is involved. Additional examples of central nervous system disorders include panic syndrome, anticipatory anxiety, phobic anxiety, panic anxiety, chronic anxiety, and endogenous anxiety.

The compounds of Formula I may further be useful in the treatment of oncologic disorders wherein CCK or gastrin may be involved. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit moisis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to cocaine, alcohol or nicotine.

The present invention also encompasses a pharmaceutical composition useful in the treatment of CCK and/or gastrin disorders comprising the administration of a therapeutically effective but non-toxic amount of the compounds of Formula I, with or without pharmaceutically acceptable carriers or diluents.

The present invention also encompasses a pharmaceutical composition useful in the treatment of CCK and/or gastrin disorders comprising the administration of a therapeutically effective but non-toxic amount of the compounds of Formula I, with or without pharmaceutically acceptable carriers or diluents.

The compounds of Formula I, may be administered to animals, preferably to mammals, and most especially to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight, administered in single or divided doses.

In some cases, however, it may be necessary to use dosage levels outside these limits. For example, doses as low as about 1 ng/kg, about 0.005 $\mu$g to about 0.05 $\mu$g or about 100 ng to about 100 $\mu$g/kg may be administered.

In the effective treatment of panic syndrome, panic disorder, anxiety disorder and the like, preferably about 0.05 mg/kg to about 0.5 mg/kg of CCK antagonist maybe administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

In the treatment of irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumor palliative for gastrointestinal neoplasma with gastrin receptors, as a modulator of central nervous activity, treatment of Zollinger-Ellison snydrome, or in the treatment of peptic ulcer disease, an effective dosage is preferably from about 0.1 to about 10 mg/kg, administered one-to-four times daily is indicated.

Because these compounds antagonize the function of CCK in animals, they may also be used as feed additives to increase the food intake of animals in daily dosage preferably from about 0.05 mg/kg to about 50 mg/kg of body weight.

the compounds of Formula I may be prepared according to the Reaction Schemes I and II as set forth below.

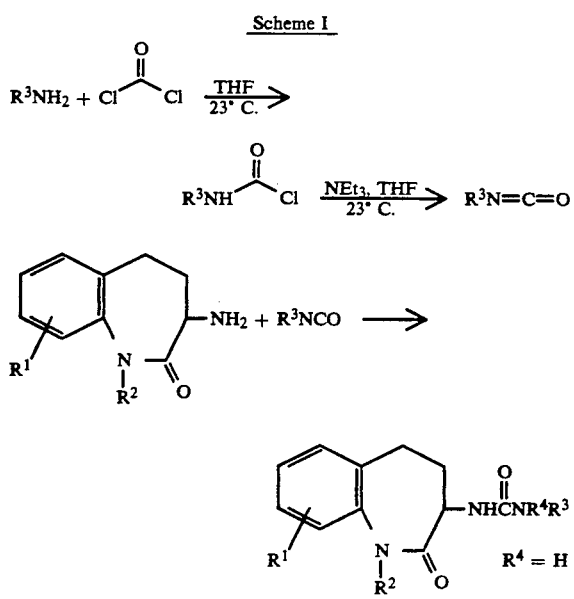

Scheme I

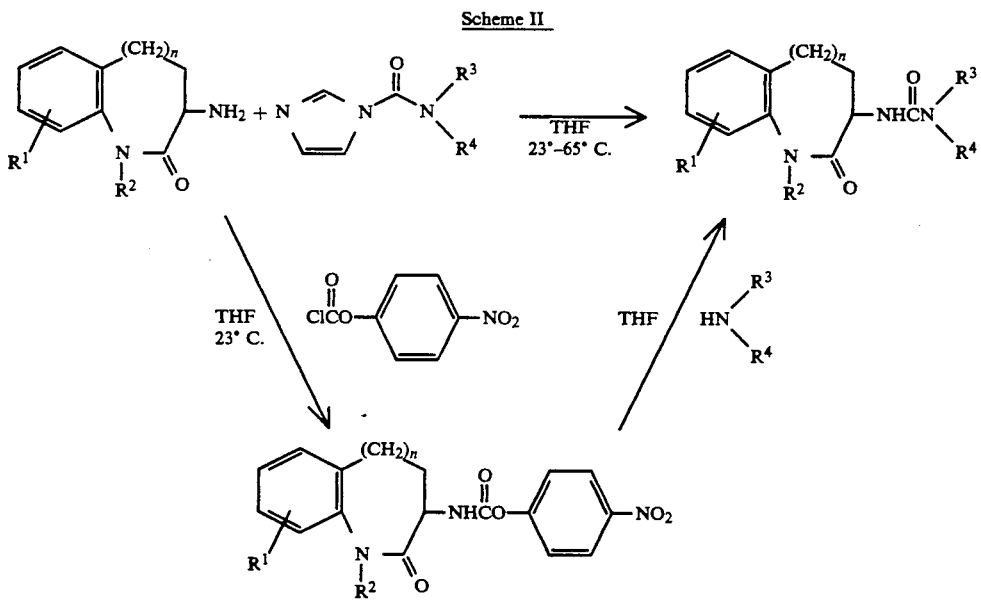

Scheme II

MATERIALS AND METHODS

1. Anxiolytic Activity of the Compounds of Formula I

The black/white exploration test [Crawley et al. Pharmacology, Biochemistry and Behav. 13, 167 (1980)] is a simple animal model of anxiety. Rodents placed in a two compartment box which consists of a brightly lit, white painted side and a dimly lit, black painted side, display a marked preference for the black side of the apparatus. This behavior is caused by the aversive properties of the brightly lit, white painted section. Classical anxiolytic drugs [such as diazepam, see Crawley, supra] and novel anxiolytic drugs [such as $5HT_3$ antagonists, see Jones et al. Br. J. Pharm. 93, 985 (1988)] decrease the preference of the animal for the black dimly lit side of the apparatus.

A. Naive male DBA2 mice (25-30) were housed on a reversed light/dark cycle and tested during the dark phase of the cycle under dim red light. The apparatus consisted of an open topped box (40 cm long×27 cm wide×27 cm high) divided into a small area (2/5) and a large area (3/5) by a partition that extended 20 cm above the walls. There was a 7.5×7.5 cm opening in the partition at floor level. The small compartment was painted black and the large compartment white. The floor of each compartment was marked into 9 cm squares. The white compartment was illuminated by a 100 W tungsten bulb 17 cm above the box and the black compartment by a similarly placed 60 W red bulb.

Animals that had been injected with drug or vehicle were placed individually into the centre of the white area and their behavior observed during a 5 minute period by remote video recording. Four behavioral parameters were recorded every minute: the number of exploratory rears in the white and black sections, the number of line crossings in the black and white sections, the number of transitions between the two sections and the time spent in the black and white sections. Animals were tested in treatment groups of 8-10 and vehicle controls were run on each test day. Data were analysed by ANOVA and Dunnetts test.

In one series of tests, the following compounds were employed:

Compound A: 3(S)-(-)-1,3-dihydro-3-(2-indolecarbonylamino)-1-methyl-5-phenyl-2H-1,4-benzodiazepin-2-one, an effective antagonist of CCK-A receptors;

Compound B: (R)-N-(2,3-dihydro-1-methyl-2-oxo-5-phenyl-1H-1,4-benzodiazepin-3-yl)-N'-(3-methylphenyl)urea, an effective antagonist of CCK-B receptors.

Vehicle treated animals displayed a marked preference for activity in the black side of the test arena, probably induced by the aversive properties of the brightly lit, white painted section. Compound A at doses of 0.05, 0.5, 5.0 and 500 ug/kg significantly decreased the preference for rearing in the black side. Similarly, 0.5, 5.0 and 500 ug/kg of Compound A abolished the preference for locomotion (line crossings) in the black side. The difference in time spent in the black and white side was abolished by 5.0 and 500 ug/kg of Compound A. Compound B at a dose of 0.05 ug/kg abolished the preference for rearing in the black side and a dose of 0.005 ug/kg decreased the difference in time spent in the black and white side.

These results demonstrate that CCK antagonists have anxiolytic properties in mice. The active dose range for Compound B (0.005–0.05 ug/kg) was lower than that for Compound A (0.05–5.0 ug/kg), suggesting that the response may be mediated by CCK-B receptors. This is consistent with studies in humans in which CCK-4 (which is a preferential CCK-B receptor agonist) was reported to induce panic, whereas CCK-8 (which is equipotent as an agonist at CCK-A and CCK-B receptors) induced gastrointestinal effects but not panic symptoms. Therefore, compounds A and B are clinically useful in the treatment of anxiety.

B. The effects of CCK-8 and compound A on the exploratory behavior of the rat were examined in automated activity cages and by direct observation. It is known that exogenous CCK-8 decreases exploratory behavior in rats in a novel environment by accelerating the process of habituation. [See Crawley, Pharm. Biochem & Behav. 20, 23–27 (1984).]

Expt 1. Male Sprague Dawley rats were injected (I.p.) with CCK-8 and immediately placed in automated activity cages. Activity was measured for 30 minutes past injection. CCK-8 (0.5–16 $\mu$g/kg) dose-dependently decreased locomotor activity $F(6,87)=3.21$ ($p<0.01$). These results confirm previous reports that CCK decreases locomotor activity in a novel environment.

Expt 2. Male SD rats were injected (s.c.) with the CCK antagonist compound A (0.0001–10 mg/kg) and immediately placed in the automated activity cages. Compound A delayed habituation and prolonged the period of exploratory activity of the rats $F(6,124)=2.54$, $p<0.05$. The drug effects were most pronounced at 25 minutes where 0.1 mg/kg induced levels of activity significantly above controls $F(6.124)=3.18$, $p<0.01$. The dose response curve was bell-shaped with higher and lower doses having no significant effect on activity at the time point. As the anxiolytic drug chlordiazepoxide also increases spontaneous locomotor activity in rats in a novel environment [(McElroy et al. *Psychopharm.* 85: 224–226 (1985)] these findings are consistent with an anxiolytic action of Compound A useful in the treatment of panic disorder.

Expt 3. In order to assess further the effect of Compound A on exploration in a novel environment, the motoric behaviors of rats placed in a perspex cage was recorded by direct observation for a 15 minute period 15 minutes after treatment with Compound A.

Experimenters (unaware of the treatments the animals had received) recorded the frequency and duration of rearing, sniffing, grooming and cage crossing using a keypad interfaced to a BBC microcomputer.

Sniffing, ($F(3,43)=3.96$, $P<0.01$) rearing ($F(3,43=4.77$, $P<0.01$) and cage crossing ($F(3,43)=3.79$, $P<0.05$) were all significantly increased by 0.1 mg/kg of Compound A. These results are consistent wit the data from the automatic activity measures (see Experiment 2) and further support the utility of compound A in the treatment of panic disorder.

2. CCK Receptor Binding (Pancreas)

CCK-33 was radiolabeled with $^{125}$I-Bolton Hunter reagent (2000 Ci/mmole) as described by Sankara et al. (J. Biol. Chem. 254: 9349–9351, 1979). Receptor binding was performed according to Innis and Snyder (Proc. Natl. Acad. Sci. 77, 6917–6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200–350 g) were sacrificed by decapitation. The whole pancreas was dissected free of fat tissue and was homogenized in 20 volumes of ice-cold 50 mM Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 $\mu$l of buffer (for total binding) or unlabeled CCK-8 sulfate to give a final concentration of 1 $\mu$M (for nonspecific binding) or the compounds of Formula I (for determination of inhibition of $^{125}$I-CCK binding) and 25 $\mu$l of $^{125}$I-CCK-33 (30,000–40,000 cpm) were added to 450 $\mu$l of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33.

3. CCK Receptor Binding (Brain)

CCK-33 was radiolabeled and the binding was performed according to the description for the pancreas method with modifications according to Saito et al., J. Neurochem. 37:483–490, 1981.

Male Hartley guinea pigs (300–500 g) were sacrificed by decapitation and the brains were removed and placed in ice-cold 50 mM Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 minutes. Pellets were resuspended in Tris Buffer, centrifuged as above and resuspended in 200 volumes of binding assay buffer (10 mM N-2-hydroxyethyl-piperazine-N'-2-ethane sulfonic acid (HEPES), 5 mM MgCl$_2$, 0.25 mg/ml bacitracin, 1 mM ethylene glycol-bis-($\beta$-aminoethylether-N,N'-tetraacetic acid) (EGTA), and 0.4% bovine serum albumin (BSA)). For the binding assay, 25 $\mu$l of buffer (for total binding) or unlabeled CCK-8 sulfate to give a final concentration of 1 $\mu$m (for nonspecific binding) or the compounds of Formula I (for determination of inhibition of $^{125}$I-CCK binding) and 25 $\mu$l of $^{125}$I-CCK-33 (30,000–40,000 cpm) were added to 450 $\mu$l of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the following assays.

4. Isolated Guinea Pig Gall Bladder

Male Hartley guinea pigs (400–600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions are recorded using Statham (60 g; 0.12 mm) strain gauges and a Hewlett-Packard (77588) recorder. The tissues are washed every 10 minutes for 1 hour to obtain equilibrium prior to the beginning of the study. CCK-8 is added cumulatively to the baths and $EC_{50}$'s determined using regression analysis. After washout (every 10 minutes for 1 hour), the compound of Formula I is added at least 5 minutes before the addition of CCk-8 and the $EC_{50}$ of CCK-8 in the presence of the compound of Formula I similarly determined.

5. Isolated Longitudinal Muscle of Guinea Pig Ileum

Longitudinal muscle strips with attached nerve plexus are prepared as described in *Brit. J. Pharmac.* 23:; 356–363, 1964; *J. Physiol.* 194: 13–33, 1969. Male Hartley guinea pigs are decapitated and the ileum removed (10 cm of the terminal ileum is discarded and the adjacent 20 cm piece used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds of Formula I determined as described in the gall bladder protocol (above).

6. Gastrin Antagonism

Gastrin antagonist activity of compounds of Formula I is determined using the following assay.

A. Gastrin Receptor Binding in Guinea Pig Gastric Glands

Preparation of Guinea Pig Gastric Mucosal Glands

Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300–500 g body weight, male Hartley) were washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

B. Binding Studies

The washed guinea pig gastric glands prepared as above were resuspended in 25 ml of standard buffer containing 0.25 mg/ml of bacitracin. For binding studies, to 220 μl of gastric glands in triplicate tubes, 10 μl of buffer (for total binding) or gastrin (1 μM final concentration, for nonspecific binding) or test compound and 10 μl of $^{125}I$-gastrin (NEN, 2200 Ci/mmole, 25 pM final) or $^3H$-pentagastrin (NEN 22 Ci/mmole, 1 nM final) were added. The tubes were aerated with 95% $O_2$ and 5% $CO_2$ and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}I$-gastrin or liquid scintillation counting for $^3H$-pentagastrin.

In Vitro Results

Effect of the Compounds of Formula I on $^{125}I$-CCK-33 Receptor Binding

The preferred compounds of Formula I are those which inhibited specific $^{125}I$-CCK-33 binding in a concentration dependent manner.

Scatchard analysis of specific $^{125}I$-CCK-33 receptor binding in the absence and presence of the compounds of Formula I indicated the compound of Formula I competitively inhibited specific $^{125}I$-CCK-33 receptor binding since it increased the $K_D$ (dissociation constant) without affecting the $B_{max}$ (maximum receptor number). A $K_i$ value (dissociation constant of inhibitor) of the compounds of Formula I was estimated.

The data of Table I were obtained for compounds of Formula I.

TABLE I

CCK RECEPTOR BINDING RESULTS $IC_{50}$ (μM)

| Compound of Ex # | $^{125}I$-CCK Pancreas | $^{25}I$-CCK Brain | $^{25}I$-Gastrin Gastric Glands |
|---|---|---|---|
| 1 | 0.35 | 0.18 | 0.12 |
| 2 | 14 | 0.062 | 0.026 |
| 3 | 2.1 | 8.6 | 3.1 |
| 4 | 0.012 | 0.052 | 0.018 |
| 5 | 0.94 | 2.2 | 2.5 |
| 6 | 0.08 | 0.062 | 0.037 |
| 7 | 0.97 | 5 | 0.61 |
| 8 | 0.96 | 0.148 | 0.48 |
| 9 | 20 | 17 | 5.5 |
| 10 | 32 | 13 | 5.4 |
| 11 | 1.7 | 0.65 | 0.46 |
| 12 | 0.17 | 0.66 | 0.13 |
| 13 | 1.6 | 1.0 | |
| 14 | 13 | 77 | |

EXAMPLES

Examples provided are intended to assist in a further understanding of the invention. Particular materials employed, species and conditions are intended to be further illustrative of the invention and not limitative of the reasonable scope thereof.

EXAMPLE 1

1,1-Dimethylethyl 3-{[[(4-chlorophenyl)amino]carbonyl]amino}-2,3,4,5-tetrahydro-2-oxo-1H-1-benzazepine-1-acetic acid ester To a solution of 2 mL of dry tetrahydrofuran containing 83 mg (0.29 mMole) of 3-amino-1-(carbo-t-butoxymethyl)-2,3,4,5-tetrahydro-1H-(1)benzazepinone was added 4-chlorophenylisocyanate (43 mg, 0.29 mMole) in one portion. The reaction mixture was allowed to stand at room temperature overnight. The reaction solvent was slowly evaporated and treated with ether to induce crystallization. The analytical product was obtained as a white solid in 75% yield: mp=194°-196° C.

TLC, HPLC: >97% pure.
FAB MS: 444 M+ +H.
$^1$HNMR (DMSO-d$_6$): Confirmed structure of the title compound.
Elemental Analysis for $C_{23}H_{26}N_3O_4Cl$. Calc'd: C, 62.23; H, 5.90; N, 9.47. Found C, 62.27; H, 6.09; N, 9.28.

EXAMPLE 2

1,1-Dimethylethyl 2,3,4,5-tetrahydro-3-{[[(3-methoxyphenyl)amino]carbonyl]-amino{-1H-1-benzazepine-1-acetic acid ester Using identical reaction conditions to those described in Example 1, 250 mg (0.87 mMole) of 3-amino-1-(carbo-t-butoxymethyl)-2,3,4,5-tetrahydro-1H-(1)benzazepinone and 3-methoxyphenylisocyanate (113 μL, 0.87 mMole) were reacted to afford the title compound in 97% yield: mp=203°-204° C.

TLC, HPLC: >96% pure.
FAB MS: 440 M+ +H, 462 M+ +Na.
$^1$HNMR (DMSO-d$_6$): Confirmed structure of the title compound.
Elemental Analysis for $C_{24}H_{29}N_3O_5$. Calc'd: C, 65.59; H, 6.65; N, 9.56. Found: C, 65.33; H, 6.75; N, 9.57.

EXAMPLE 3

2,3,4,5-Tetrahydro-3-{[[(3-methoxyphenyl)amino]carbonyl]amino{-2-oxo-1H-1-benzazepine-1-acetic acid Hydrogen chloride gas was passed into an ice cold solution of 50 mL of ethyl acetate containing 300 mg of 1,1-dimethylethyl-2,3,4,5-tetrahydro-3-{[[(3-methoxyphenyl)amino]carbonyl]amino}-1H-1-benzazepine-1-acetic acid ester. After 2 hours, the solvent and excess hydrogen chloride gas were rotoevaporated under reduce pressure to give a pale yellow solid. Trituration with ethyl acetate afforded 260 mg (100% yield) of the analytical sample: mp=213°-215° C.

TLC, HPLC: >97% pure.
FAB MS: 384 M+ +H, 406 M+ +Na.
$^1$HNMR (DMSO-d$_6$): Confirmed structure of the title compound.
Elemental Analysis for $C_{20}H_{21}N_3O_5 \cdot 0.3$ $C_4H_9O_2$. Calc'd: C, 62.13; H, 5.75; N, 10.25. Found C, 61.83; H, 5.85; N, 10.54.

EXAMPLE 4

1,1-Dimethylethyl 2,3,4,5-tetrahydro-3-{[[(3-methylphenyl)amino]carbonyl]-amino}-1H-1-benzazepine-1-acetic acid ester Using identical reaction conditions to those described in Example 1, 250 mg (0.87 mMole) of 3-amino-1-(carbo-t-butoxymethyl)-2,3,4,5-tetrahydro-1H-(1)benzazepinone and 3-methylphenylisocyanate (110 μL, 0.87 mMole) were reacted to afford the title compound.

Preparative thick layer chromatography of the crude reaction product (chloroform-methanol, 99:1, v/v) and recrystallization from ethyl acetate afforded the analytical product: mp=169°-171° C.

TLC, HPLC: >99% pure.
FAB MS: 424 M+ +H.
$^1$HNMR (DMSO-d$_6$): Confirmed structure of the title compound.
Elemental Analysis for $C_{24}H_{29}N_3O_4 \cdot 0.5$ $C_4H_8O_2$. Calc'd: C, 66.79; H, 7.11; N, 8.99. Found: C, 66.94; H, 7.11; N. 9.02.

EXAMPLE 5

2,3,4,5-Tetrahydro-3-{[[(3-methylphenyl)aminol]carbonyl]amino}-2-oxo-1H-1-benzazepine-1-acetic acid Hydrogen chloride gas was passed into an ice cold solution of 50 mL of ethyl acetate containing 200 mg of 1,1-dimethylethyl 2,3,4,5-tetrahydro-3-{[[(3-methoxyphenyl)amino]carbonyl]amino}-1H-1-benzazepine-1-acetic acid ester. After 2 hours, the solvent and excess hydrogen chloride gas were rotoevaporated under reduced pressure to give 200 mg of a pale yellow solid. Trituration with ethyl acetate and recrystallization from methanol yielded the analytical sample: mp=230°-231° C.

TLC, HPLC: >98% pure.
FAB MS: 368 M+ +H.
$^1$HNMR (DMSO-d$_6$): Confirmed structure of the title compound.
Elemental Analysis for $C_{20}H_{21}N_3O_4 \cdot 0.35$ $H_2O$. Calc'd: C, 62.13; H, 5.75; N, 10.25. Found: C, 61.83; H, 5.85; N, 10.54.

EXAMPLE 6

1-{[2,3,4,5-Tetrahydro-3-{[[(3-methylphenyl)amino]carbonyl]amino}-2-oxo-1H-1-benzazepin-1-yl]acetyl} pyrrolidine 2,3,4,5-Tetrahydro-3-{[[(3-methylphenyl) amino]carbonyl]amino}-2-oxo-1H-1-benzazepin-1-acetic acid (80 mg, 0.22 mMole) in 3 mL of dry N,N-dimethylformamide was combined with 1-ethyl-3-(3-dimethylaminopropyl)carbodiimide.HCl (58 mg, 0.30 mMole), 1-hydroxybenzotriazole hydrate (41 mg, 0.30 mMole) and pyrrolidine (58 μL, 0.58 mMole) at room temperature. The resulting reaction mixture was stirred for 1 hour and concentrated in vacuo. The residue was partitioned between ethyl acetate (60 mL) and water (10 mL). The phases were separated and the organic phase was dried over anhydrous sodium sulfate. Slow evaporation of the organic extracts afforded a solid which was chromatographed on silica gel (chloroform-methanol-concentrated ammonium hydroxide, 95:5:0.5, v/v) to give the analytical product after trituration with methanol: mp=268°-270° C.

TLC, HPLC: >99% pure.
FAB MS: 420 M+.
$^1$HNMR (DMSO-d$_6$): Confirmed structure of the title compound.
Elemental Analysis for $C_{24}H_{28}N_4O_3 \cdot 0.15$ $H_2O$. Calc'd: C, 68.11; H, 6.74; N, 13.24. Found: C, 68.13; H, 6.56; N, 13.26.

EXAMPLE 7

1-Methyl-4-{[2,3,4,5-tetrahydro-3-{[[(3-methylphenyl)amino]carbonyl]amino}-2-oxo-1H-1-benzazepin-1-yl]aceyl}piperazine Using identical reaction conditions to those described in Example 6, 2,3,4,5-Tetrahydro-3-{[[(3-methylphenyl)amino]-carbonyl]amino}-2-oxo-1H-1-benzazepine-1-acetic acid (80 mg, 0.22 mMole) in 3 mL of dry N,N-dimethylformanide was combined with 1-ethyl-(3-dimethylaminopropyl) carbodiimide.HCl (58 mg, 0.30 mMole), 1-hydroxybenzotriazole hydrate (41 mg, 0.30 mMole) and N-methyl piperazine (55 µL, 0.50 mMole) to yield 98 mg of a white solid. Trituration of the crude product with methanol-ethyl acetate (2:1, v/v) gave the analytical sample: mp=228°-229° C.

TLC, HPLC: >98% pure.
FAB MS: 450 M+ +H.
$^1$HNMR (DMSO-d$_6$): Confirmed structure of the title compound.
Elemental Analysis for $C_{25}H_{31}N_5O_3.0.25$ $H_2O$. Calc'd: C, 66.13; H, 6.99; N, 15.43. Found: C, 66.11; H, 6.61; N, 15.51.

EXAMPLE 8

1,1-Dimethylethyl 2,3,4,5-tetrahydro-3-{[[(1-naphthalenyl)amino]carbonyl]-amino}-1H-1-benzazepine-1-acetic acid ester Using identical reaction conditions to those described in Example 1, 300 mg (1.02 mMole) of 3-amino-1-(carbo-t-butoxymethyl)-2,3,4,5-tetrahydro-1H-(1)benzazepinone and 1-naphthylisocyanate (147 µL, 1.02 mMole) were reacted to afford the title compound. Preparative thick layer chromatography of the crude reaction product (chloroform-methanolconcentrated ammonium hydroxide, 98:2:0.2, v/v) and recrystallization from ethyl acetate afforded the analytical product: mp=225°-226° C.

TLC, HPLC: >98% pure.
FAB MS: 459 M+.
$^1$HNMR (DMSO-d$_6$): Confirmed structure of the title compound.
Elemental Analysis for $C_{27}H_{29}N_3O_4.0.25$ $H_2O$. Calc'd: C, 69.88; H, 6.41; N, 9.06. Found: C, 69.84; H, 6.45 N, 8.88.

EXAMPLE 9

2,3,4,5-Tetrahydro-3-{[[(1-naphthalenyl)amino]carbonyl]amino}-2-oxo-1H-1-benzazepine-1-acetic acid Using identical reaction conditions to those described in Example 3, 1,1-dimethylethyl 2,3,4,5-tetrahydro-3-{[[(1-naphthalenyl)amino]carbonyl]amino}-1H-1-benzazepine-1-acetic acid ester (240 mg) was converted to the title compound in essentially quantitative yield. The analytical sample was obtained by recrystallization of the crude reaction product from methanol: mp=215°-216° C.

TLC, HPLC: >99% pure.
FAB MS: 404 M+ +H.
$^1$HNMR (DMSO-d$_6$): Confirmed structure of the title compound.
Elemental Analysis for $C_{23}H_{21}N_3O_4.0.4$ $H_2O.0.9$ $CH_3OH$. Calc'd: C, 65.31; H, 5.83; N, 9.56. Found: C, 65.31; H, 5.62; N, 9.54.

EXAMPLE 10

1-Methyl-4-{[2,3,4,5-tetra-hydro-3-{[[(1-naphthalenyl)amino]carbonyl]amino}-2-oxo-1H-1-benzazepin-1-yl]acetyl}piperazine Using identical reaction conditions to those described in Example 6, 2,3,4,5-tetrahydro-3-{[[(1-naphthalenyl)amino]-carbonyl]amino}-2-oxo-1H-1-benzazepine-1-acetic acid (190 mg, 0.47 mMole) in 4 mL of dry N,N-dimethylformamide was combined with 1-ethyl-3-(3-dimethylaminopropyl)carbodiimide.HCl (126 mg, 0.66 mMole), 1-hydroxybenzotriazole hydrate (89 mg, 0.66 mMole) and N-methyl piperazine (104 µL, 0.94 mMole) to yield 390 mg of a waxy oil. Crystallization of the crude product from methanol-ethyl acetate (2:1, v/v) gave the analytical sample: mp=288°-290° C.

TLC, HPLC: >95% pure.
FAB MS: 486 M+ +H.
$^1$HNMR (DMSO-d$_6$): Confirmed structure of the title compound.
Elemental Analysis for $C_{28}H_{31}N_5O_3.0.25$ $H_2O$. Calc'd: C, 68.62; H, 6.48; N, 14.29. Found: C, 68.59; H, 6.36; N, 14.22.

EXAMPLE 11

1-{[2,3,4,5-Tetrahydro-3-{[[(1-naphthalenyl)amino]carbonyl]amino}-2-oxo-1H-1-benzazepin-1-yl]acetyl}pyrrolidine Using identical reaction conditions to those described in Example 6, 2,3,4,5-tetrahydro-3-{[[(1-naphthalenyl)amino]carbonyl]amino}-2-oxo-1H-1-benzazepine-1-acetic acid (190 mg, 0.47 mMole) in 4 mL of dry N,N-dimethylformamide was combined with 1-ethyl-3-(3-dimethylaminopropyl)carbodiimide.HCl (126 mg, 0.66 mMole), 1-hydroxybenzotriazole hydrate (89 mg, 0.66 mMole) and pyrrolidine (79 µL, 0.94 mMole) to yield 390 mg of a waxy oil. Crystallization of the crude product from methanol-ethyl acetate (2:1, v/v) gave the analytical sample: mp=285°-287° C.

TLC, HPLC: >95% pure.
FAB MS: 457 M+ +H.
$^1$HNMR (DMSO-d$_6$): Confirmed structure of the title compound.
Elemental Analysis for $C_{27}H_{28}N_4O_3$. Calc'd: C, 71.03; H, 6.18; N, 12.27. Found: C, 70.86; H, 6.02; N, 12.23.

EXAMPLE 12

1,1-Dimethylethyl 2,3,4,5-tetrahydro-3-{[[(4-methylphenyl)amino]carbonyl]amino}-1H-1-benzazepine-1-acetic acid ester Using identical reaction conditions to those described in Example 1, 245 mg (0.85 mMole) of 3-amino-1-(carbo-t-butoxymethyl)-2,3,4,5-tetrahydro-1H-(1)benzazepinone and 4-methylphenylisocyanate (107 µL, 0.85 mMole) were reacted to afford the title compound. Preparative thick layer chromatography of the crude reaction product on silica gel (chloroform-methanol, 97:3, v/v) afforded the analytical product: mp=181°-183° C.

TLC, HPLC: >98% pure.
FAB MS: 424 M+.
$^1$HNMR (DMSO-d$_6$): Confirmed structure of the title compound.

Elemental Analysis for $C_{24}H_{29}N_3O_4 \cdot 0.35\ H_2O$. Calc'd: C, 67.06; H, 6.97; N, 9.78. Found: C, 67.01; H, 6.68 N, 9.75.

EXAMPLE 13

1-{[2,3,4,5-Tetrahydro-3-{[[(4-methylphenyl)amino]-carbonyl]amino}-2-oxo-1H-1-benzazepin-1-yl]aceyl} pyrrolidine Using identical reaction conditions to those described in Example 6, 2,3,4,5-tetrahydro-3-{[[(4-methylphenyl)amino]carbonyl]amino}-2-oxo-1H-1-benzazepine-1-acetic acid (83 mg, 0.22 mMole) in 3 mL of dry N,N-dimethylformamide was combined with 1-ethyl-3-(3-dimethylaminopropyl)carbodiimide.HCl (58 mg, 0.30 mMole), 1-hydroxybenzotriazole hydrate (41 mg, 0.30 mMole) and pyrrolidine (50 μL, 0.58 mMole) to yield approximately 100 mg of a white powder. Recrystallization of the crude product from methanol-ethyl acetate (1:3, v/v) gave the analytical sample as white crystals: mp=279°–281° C.

TLC, HPLC: >99% pure.

FAB MS: 421 M+H.

$^1$HNMR (DMSO-d$_6$): Confirmed structure of the title compound.

Elemental Analysis for $C_{24}H_{28}N_4O_3$. Calc'd: C, 68.55; H, 6.71; N, 13.32. Found: C, 68.84; H, 6.77; N, 13.34.

EXAMPLE 14

1-Methyl-4-{[2,3,4,5-tetra-hydro-3-{[[(4-methylphenyl)amino}carbonyl]amino}-2-oxo-1H-1-benzazepin-1-yl]acetyl}piperazine Using identical reaction conditions to those described in Example 6, 2,3,4,5-tetrahydro-3-{[[(4-methylphenyl)amino]-carbonyl]amino}-2-oxo-1H-1-benzazepine-1-acetic acid (83 mg, 0.22 mMole) in 3 mL of dry N,N-dimethyl-formamide was combined with 1-ethyl-3-(3-dimethyl-aminopropyl)carbodiimide.HCl (58 mg, 0.03 mMole), 1-hydroxybenzotriazole hydrate (41 mg, 0.30 mMole) and N-methyl piperazine (55 μL, 0.50 mMole) to yield approximately 170 mg of crude product. Chromatography of the crude product on silica gel (chloroform-methanol-concentrated ammomium hydroxide (92:8:0.8, v/v) gave a white solid which was recrystallized from methanol:ethyl acetate (1:, v/v) to yield the analytical sample as white crystals: mp=257°–259° C.

TLC, HPLC: >99% pure.

FAB MS: 450 M++H.

$^1$HNMR (DMSO-d$_6$): Confirmed structure of the title compound.

Elemental Analysis for $C_{25}H_{31}N_5O_3 \cdot 0.3\ H_2O$. Calc'd: C, 66.26; H, 6.98; N, 15.46. Found: C, 66.18; H, 6.78; N, 15.45.

What is claimed is:

1. A compound of Formula I:

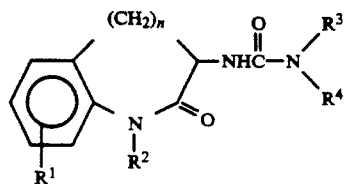

wherein:

$R^1$ is H, halo, hydroxy, nitro, amino, cyano, $C_1$–$C_8$-alkyl, $C_1$–$C_4$-alkylamino, $C_1$–$C_4$-alkoxy;

$R^2$ is unsubstituted or mono-, di-, or trisubstituted $C_1$–$C_8$-straight- or branched-alkyl, where the substituents are selected from the group consisting of $C_1$–$C_4$-alkylthio, $C_1$–$C_4$-alkyloxy, $C_1$–$C_4$-alkylamino, unsubstituted or mono-, di-, or trisubstituted phenyloxy or naphthyloxy unsubstituted or mono-, di-, or trisubstituted phenylthio or naphthylthio, unsubstituted or mono-, di-, or trisubstituted phenyl or naphthyl, and the substituents on the phenyloxy or naphtholoxy, the phenylthio or naphthylthio, the $C_6$- or $C_{10}$-aryl being selected from $C_1$–$C_8$-straight- or branched-alkyl, hydroxy, $C_1$–$C_4$-alkoxy, halo, nitro, amino, $C_1$–$C_4$-alkylthio or mono- or di-$C_1$–$C_4$-alkylamino; substituted carbonyl-$C_1$–$C_4$-alkyl, which carbonyl group is substituted with hydroxy, $C_1$–$C_8$-straight- or branched-alkoxy, $C_1$–$C_8$-straight- or branchedalkyl, unsubstituted or mono-, di-, or trisubstituted phenyl or naphthyl, unsubstituted or mono-, di-, or trisubstituted phenyl or naphthyl-$C_1$–$C_8$-alkyl, and unsubstituted or mono-, di-, or trisubstituted phenyl or naphthyl-$C_1$–$C_4$-alkoxy, where the substituents on the phenyl or naphthyl, the phenyl or naphthyl-$C_8$-alkyl or the phenyl or naphthyl-$C_1$–$C_4$-alkoxy are selected from the groups consisting of hydroxy, $C_1$–$C_8$-straight-or branched-alkyl, $C_1$–$C_4$-alkoxy, halo, cyano, nitro, amino, $C_1$–$C_4$-alkylthio, and mono- or di-$C_1$–$C_4$- alkylamino, or $NR^6R^7$, where $R^6$ and $R^7$ are independently selected from hydrogen, $C_1$–$C_6$-straight- or branched-alkyl, unsubstituted or mono-, di-, or trisubstituted-carboxy-$C_1$–$C_8$-straight- or branched-alkyl, or unsubstituted or mono-, di-, or trisubstituted-carboxamido-$C_1$–$C_8$-straight- or branched-alkyl, wherein the substituents on the carboxy-$C_1$–$C_8$-straight- or branched-alkyl or on the carboxamido-$C_1$–$C_8$-straight- or branched-alkyl are selected from the group consisting of unsubstituted or mono-, di-, or trisubstituted phenyl or naphthyl, unsubstituted or mono-, di- or trisubstituted phenyl or naphthyl-$C_1$–$C_8$-alkyl, unsubstituted or mono-, di-, or trisubstituted phenyl or naphthyl-$C_{10}$-aryl-$C_1$–$C_4$-alkoxy, where the substituents on the phenyl or naphthyl, the phenyl or naphthyl-$C_1$–$C_8$-alkyl or the phenyl or naphthyl-$C_1$–$C_4$-alkoxy are selected from the group consisting of hydroxy, $C_1$–$C_8$-straight- or branched-alkyl, $C_1$–$C_4$-alkoxy, halo, nitro, cyano, amino, $C_1$–$C_4$-alkylthio, and mono- or di-$C_1$–$C_4$-alkylamino;

$R^3$ and $R^4$ are independently unsubstituted or mono-, di- or trisubstituted phenyl or naphthyl, where the substituents are selected from the group consisting of $C_1$–$C_8$-straight- or branched-alkyl, hydroxy, $C_1$–$C_4$-alkoxy, halo, nitro, amino, cyano, $C_1$–$C_4$-alkylthio and mono-or di-$C_1$–$C_4$-alkylamino; $C_3$–$C_{10}$-cycloalkyl; $C_3$–$C_{10}$-cycloalkyl-$C_1$–$C_4$-alkyl; $C_1$–$C_6$-straight- or branched-alkyl-Q-$(CH_2)_m$, where m is 2 to 4 and Q is O, S, SO, SO$_2$, —HC=CH—, or substituted amino, wherein the substituent is hydrogen, $C_1$–$C_8$-straight- or branched-alkyl, unsubstituted or mono-, di- or trisubstituted $C_6$- or $C_{10}$-aryl, or $C_9$–$C_{12}$-benzofused cycloalkyls;

n is 0–3;

or the optical isomers or pharmaceutically acceptable salts thereof.

2. A method of antagonizing the binding of cholecystokinin to cholecystokinin receptors which comprises contacting said cholecystokinin receptors with a therapeutically effective but non-toxic amount of a compound of claim 1 to a mammal.

3. A method of antagonizing the binding of gastrin to gastrin receptors which comprises contacting said gastrin receptors with a therapeutically effective but non-toxic amount of a compound of claim 1 to a mammal.

4. A method of treating panic disorders or other neurological disorders involving anxiety, comprising administering a therapeutically effective but non-toxic amount of a compound of claim 1.

5. A method for directly inducing analgesia, anesthesia or loss of sensation of pain, comprising a pharmaceutically acceptable carrier, and dispersed therein, a therapeutically effective but non-toxic amount of a compound of claim 1.

6. A method of treating gastrointestinal diseases in a mammal in need thereof, which comprises administering a therapeutically effective but non-toxic quantity of the compound of claim 1.

7. A method of treating oncologic disorders in a mammal in need thereof, which comprises administering a therapeutically effective but non-toxic quantity of the compound of claim 1.

8. A method for preventing or treating the withdrawal response produced by chronic treatment or abuse of drugs or alcohol in a mammal in need thereof, which comprises administering a therapeutically effective but non-toxic quantity of the compound of claim 1.

9. A method of inducing miosis following intraocular examinations or surgery in a mammal in need thereof, which comprises administering a therapeutically effective but non-toxic quantity of the compound of claim 1.

10. A method of inducing analgesia in a mammal in need thereof, which comprises administering a therapeutically effective but non-toxic quantity of the compound of claim 1.

11. A pharmaceutical composition having cholecystokinin antagonist activity comprising a pharmaceutically acceptable carrier and, dispersed therein, a therapeutically effective but non-toxic amount of a compound of claim 1.

12. A pharmaceutical composition having gastrin antagonist activity comprising a pharmaceutically acceptable carrier and, dispersed therein, a therapeutically effective but non-toxic amount of a compound of claim 1.

13. A pharmaceutical composition useful in the treatment of panic disorder or other neurological disorders involving anxiety, comprising a pharmaceutically acceptable carrier and, dispersed therein, a therapeutically effective but non-toxic amount of a compound of claim 1.

14. A pharmaceutical composition useful for directly inducing analgesia, anesthesia or loss of sensation of pain, comprising a pharmaceutically acceptable carrier and, dispersed therein, a therapeutically effective but non-toxic amount of a compound of claim 1.

15. A pharmaceutical composition useful in the treatment of gastrointestinal diseases, comprising a pharmaceutically acceptable carrier and, dispersed therein, a therapeutically effective but non-toxic amount of a compound of claim 1.

16. A pharmaceutical composition useful for treating oncologic disorders, comprising a pharmaceutically acceptable carrier and, dispersed therein, a therapeutically effective but non-toxic amount of a compound of claim 1.

17. A pharmaceutical composition useful for preventing or treating the withdrawal response produced by chronic treatment or abuse of drugs or alcohol, comprising a pharmaceutically acceptable carrier and, dispersed therein, a therapeutically effective but non-toxic amount of a compound of claim 1.

18. A pharmaceutical composition useful inducing miosis following intraocular examinations or surgery, comprising a pharmaceutically acceptable carrier and, dispersed therein, a therapeutically effective but non-toxic amount of a compound of claim 1.

19. A pharmaceutical composition useful in the treatment of panic disorder or other neurological disorders involving anxiety, comprising a pharmaceutically acceptable carrier and, dispersed therein, a therapeutically effective but non-toxic amount of a CCK and/or gastrin antagonist compound which is 1,1-Dimethylethyl 3-{[[(4-chlorophenyl)amino]carbonyl]amino}-2,3,4,5-tetrahydro-2-oxo-1H-1-benzazepine-1-acetic acid ester;

1,1-Dimethylethyl 2,3,4,5-tetrahydro-3-{[[(3-methoxyphenyl)amino]carbonyl]-amino}-1H-1-benzazepine-1-acetic acid ester;

2,3,4,5-Tetrahydro-3-{[[(3-methoxyphenyl)amino] carbonyl]amino}-2-oxo-1H-1-benzazepine-1-acetic acid;

1,1-Dimethylethyl 2,3,4,5-tetrahydro-3-{[[(3-methylphenyl)amino]carbonyl]-amino}1H-1-benzazepine-1-acetic acid ester;

2,3,4,5-Tetrahydro-3-{[[(3-methylphenyl)amino] carbonyl]amino}-2-oxo-1H-1-benzazepine-1-acetic acid;

1-{[2,3,4,5-Tetrahydro-3-{[[(3-methylphenyl)amino] carbonyl]amino}-2-oxo-1H-1-benzazepin-1-yl]acetyl}pyrrolidine;

1-Methyl-4-{[2,3,4,5-tetrahydro-3-}[[(3-methylphenyl)amino]carbonyl]amino}-2-oxo-1H-1-benzazepin-1-yl]acetyl}piperazine;

1,1-Dimethylethyl 2,3,4,5-tetrahydro-3-{[[(1-naphthalenyl)amino]carbonyl]-amino}-1H-1-benzazepine-1-acetic acid ester;

2,3,4,5-tetrahydro-3-{[[(1-naphthalenyl)amino] carbonyl]amino}-2-oxo-1H-1-benzazepine-1-acetic acid;

1-Methyl-4-{[2,3,4,5-tetrahydro-3-{[[(1-naphthalenyl)amino]carbonyl]amino}-2-oxo-1H-1-benzazepin-1-yl]acetyl}piperazine;

1-{[2,3,4,5-Tetrahydro-3-{[[(1-naphthalenyl)amino] carbonyl]amino}-2-oxo-1H-1-benzazepin-1-yl]acetyl}pyrrolidine;

1,1-Dimethylethyl 2,3,4,5-tetrahydro-3-{[[(4-methylphenyl)amino]carbonyl]amino}-1H-1-benzazepine-1-acetic acid ester;

1-{[2,3,4,5-Tetrahydro-3-{[[(4-methylphenyl)amino] carbonyl]amino}-2-oxo-1H-1-benzazepin-1-yl]acetyl}pyrrolidine;

1-Methyl-4-{[2,3,4,5-tetrahydro-3-{[[(4-methylphenyl)amino}carbonyl]amino}-2-oxo-1H-1-benzazepin-1-yl] acetyl}piperazine.

20. A pharmaceutical composition useful for directly inducing analgesia, anesthesia or loss of sensation of pain, comprising a pharmaceutically acceptable carrier and, dispersed therein, a therapeutically effective but non-toxic amount of a CCK and/or gastrin antagonist compound which is 1,1-Dimethylethyl 3-{[[(4-chlorophenyl)amino]carbonyl] amino}-2,3,4,5-tetrahydro-2-oxo-1H-1-benzazepine-1-acetic acid ester;

1,1-Dimethylethyl 2,3,4,5-tetrahydro-3-{[[(3-methoxyphenyl)amino]carbonyl]-amino}-1H-1-benzazepine-1-acetic acid ester;

2,3,4,5-Tetrahydro-3-{[[(3-methoxyphenyl)amino] carbonyl]amino}-2-oxo-1H-1-benzazepine-1-acetic acid;

1,1-Dimethylethyl 2,3,4,5-tetrahydro-3-{[[(3-methylphenyl)amino]carbonyl]-amino}-1H-1-benzazepine-1-acetic acid ester;

2,3,4,5-Tetrahydro-3-{[[(3-methylphenyl)amino] carbonyl]amino}-2-oxo-1H-1-benzazepine-1-acetic acid;

1-{[2,3,4,5-Tetrahydro-3-{[[(3-methylphenyl)amino] carbonyl]amino}-2-oxo-1H-1-benzazepin-1-yl]acetyl}pyrrolidine;

1-Methyl-4-{[2,3,4,5-tetrahydro-3-}[[(3-methylphenyl)amino]carbonyl]amino}-2-oxo-1H-1-benzazepin-1-yl]acetyl}piperazine;

1,1-Dimethylethyl 2,3,4,5-tetrahydro-3-{[[(1-naphthalenyl)amino]carbonyl]-amino}-1H-1-benzazepine-1-acetic acid ester;

2,3,4,5-Tetrahydro-3-{[[(1-naphthalenyl)amino] carbonyl]amino}-2-oxo-1H-1-benzazepine-1-acetic acid;

1-Methyl-4-{[2,3,4,5-tetrahydro-3-{[[(1-naphthalenyl)amino]carbonyl]amino}-2-oxo-1H-1-benzazepin-1-yl]acetyl}piperazine;

1-{[2,3,4,5-Tetrahydro-3-{[[(1-naphthalenyl)amino] carbonyl]amino}-2-oxo-1H-1-benzazepin-1-yl]acetyl}pyrrolidine; 1,1-Dimethylethyl 2,3,4,5-tetrahydro-3-{[[(4-methylphenyl)amino]carbonyl]amino}-1H-1-benzazepine-1-acetic acid ester;

1-{[2,3,4,5-Tetrahydro-3-{[[(4-methylphenyl)amino] carbonyl]amino}-2-oxo-1H-1-benzazepin-1-yl]acetyl}pyrrolidine;

1-Methyl-4-{[2,3,4,5-tetrahydro-3-{[[(4-methylphenyl) amino]carbonyl]amino}-2-oxo-1H-1-benzazepin-1-yl] acetyl}piperazine.

21. The compound of claim 1 which is

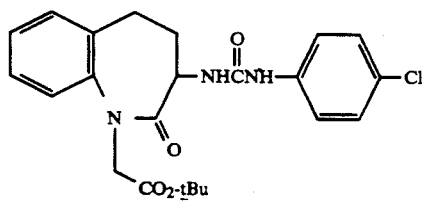

or a pharameutically acceptable salt thereof.

22. The compound of claim 1 which is

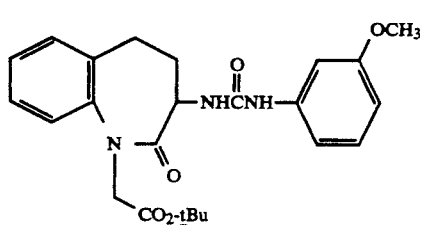

or a pharmaceutically acceptable salt thereof.

23. The compound of claim 1 which is

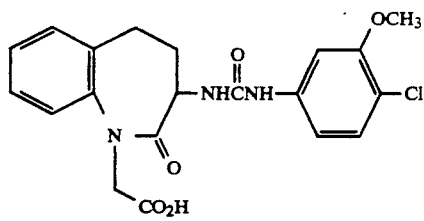

or a pharmaceutically acceptable salt thereof.

24. The compound of claim 1 which is

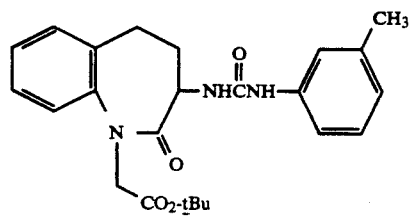

or a pharmaceutically acceptable salt thereof.

25. The compound of claim 1 which is

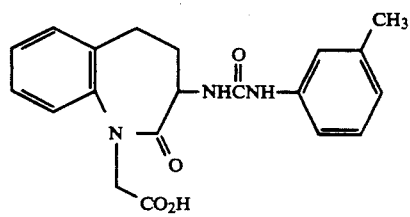

or a pharmaceutically acceptable salt thereof.

26. The compound of claim 1 which is

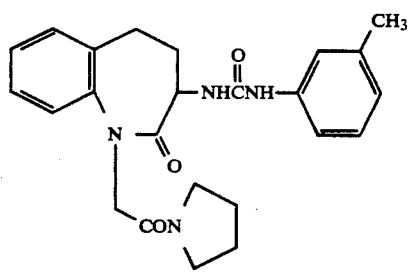

or a pharmaceutically acceptable salt thereof.

27. The compound of claim 1 which is

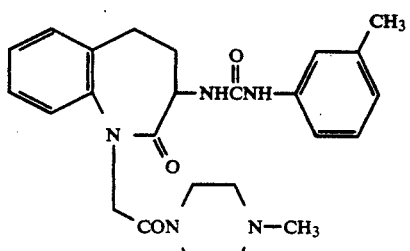

or a pharmaceutically acceptable salt thereof.

28. The compound of claim 1 which is

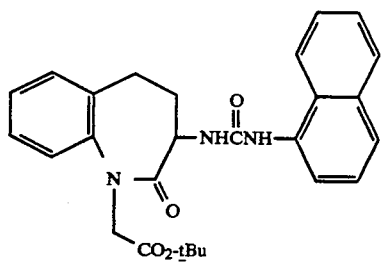

or a pharmaceutically acceptable salt thereof.

29. The compound of claim 1 which is

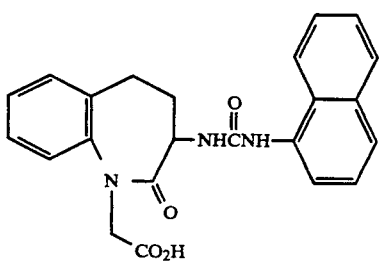

or a pharmaceutically acceptable salt thereof.

30. The compound of claim 1 which is

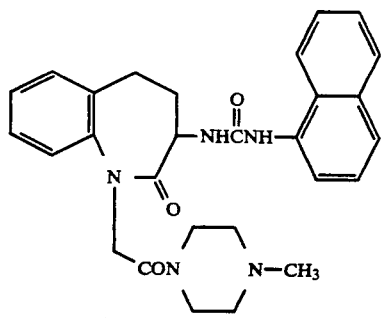

or a pharmaceutically acceptable salt thereof.

31. The compound of claim 1 which is

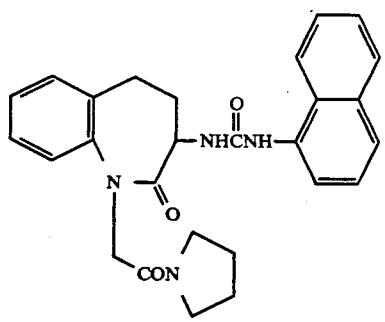

or a pharmaceutically acceptable salt thereof.

32. The compound of claim 1 which is

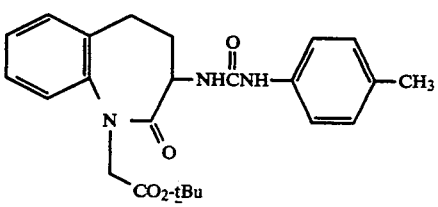

or a pharmaceutically acceptable salt thereof.

33. The compound of claim 1 which is

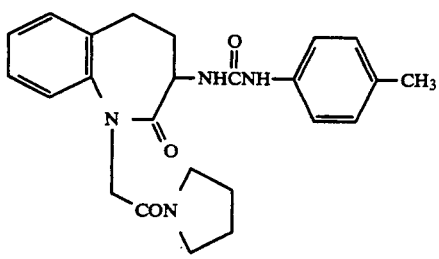

or a pharmaceutically acceptable salt thereof.

34. The compound of claim 1 which is

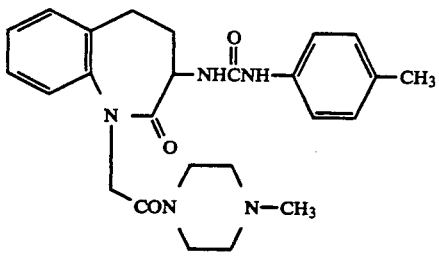

or a pharmaceutically acceptable salt thereof.

* * * * *